United States Patent [19]

Kidwell

[11] 3,994,984

[45] Nov. 30, 1976

[54] PROCESS FOR REMOVAL OF CHLOROMETHYL ETHER IMPURITIES FROM ALKYLBENZYL CHLORIDES

[75] Inventor: Roger L. Kidwell, St. Louis, Mo.

[73] Assignee: Monsanto Company, St. Louis, Mo.

[22] Filed: May 9, 1975

[21] Appl. No.: 576,068

[52] U.S. Cl. .......................................... 260/651 R
[51] Int. Cl.$^2$ ............................................ C07C 25/14
[58] Field of Search ................. 260/651 R, 651 HA

[56] References Cited
UNITED STATES PATENTS 2,620,353  12/1952  Lippincott et al. ............. 260/651 R
2,714,125  7/1955   Gerner .......................... 260/651 HA

*Primary Examiner*—D. Horwitz
*Attorney, Agent, or Firm*—N. E. Willis; J. E. Maurer; H. B. Roberts

[57] ABSTRACT

Chloromethyl ether impurities are removed from alkylbenzyl chlorides containing the same by treatment with an aqueous base.

4 Claims, No Drawings

PROCESS FOR REMOVAL OF CHLOROMETHYL ETHER IMPURITIES FROM ALKYLBENZYL CHLORIDES

BACKGROUND OF THE INVENTION

The present invention relates to a process for removal of chloromethyl ethers from alkylbenzyl chlorides containing the same.

Alkylbenzyl chlorides are well-known compounds useful in a variety of applications. For example, alkylbenzyl chlorides are useful intermediates for formation of quaternary amine compounds having utility as disinfectants, emulsifiers, antistatic agents, etc.

Alkylbenzyl chlorides, when prepared according to conventional procedures (for example, chloromethylation of alkylbenzene as described in U.S. Pat. No. 2,630,439), frequently contain chloromethyl ethers such as bis chloromethyl ether, chloromethyl methyl ether, chloromethyl ethyl ether, chloromethyl butyl ether, etc., as impurities. Such impurities have known undesirable properties and the removal of such impurities by conventional methods such as distillation is expensive and, in some instances, incomplete. Thus, an effective method of removing such impurities is desired by those skilled in the art.

SUMMARY OF THE INVENTION

It is an object of the present invention to provide a method of removing chloromethyl ether impurities from alkylbenzyl chlorides containing the same. This is accomplished by treatment with an inorganic base in a manner which will be understood from the following description of the preferred embodiment.

DESCRIPTION OF THE PREFERRED EMBODIMENTS

The process of the present invention is suited for removal of chloromethyl ether impurities from alkylbenzyl chlorides wherein the alkyl group contains at least 9 carbon atoms.

In accordance with the process of the present invention, the alkylbenzyl chloride containing the chloromethyl ether impurities is contacted with an aqueous solution of an inorganic base such as an alkali metal hydroxide carbonate or bicarbonate. The use of alkali metal hydroxides, particularly sodium hydroxide, is preferred. Preferably, the solution will be sufficiently dilute (0.1% to 50% by weight) so as not to inhibit dissolution of products of the reaction between the base and chloromethyl ethers into the aqueous medium. The quantity of aqueous base solution utilized will preferably be at least stoichiometrically sufficient to react with all chloromethyl ether impurities contained in the alkylbenzyl chloride.

The contact should be effected at a temperature of at least 25° C. to provide acceptably rapid reaction rates but below a temperature at which substantial amounts of chloromethyl ether impurities would be lost by volatilization from the reaction medium. If desired, pressure vessels or reflux condenses (to prevent loss of volatilized chloromethyl ethers) can be employed to permit use of higher temperature to obtain more rapid reaction rates.

The reaction mixture should, preferably be agitated to ensure complete contact and reaction.

It is highly unexpected that such a process could be employed for treatment of alkylbenzyl chlorides without substantial decomposition thereof since alkylbenzyl chlorides are quite reactive and many are known to decompose in contact with water or bases.

After completion of the reaction, an aqueous phase containing the products of the reaction between the base and chloromethylethers is separated from the alkylbenzyl chloride.

The practice of the invention is further illustrated by the following example.

EXAMPLE I

A chloromethylation reagent is prepared by slowly adding chlorosulfonic acid to a suspension of paraformaldehyde in absolute alcohol (mole ratio of alcohol to formaldehyde = 1.2; sufficient chlorosulfonic acid is added to provide an acid to alcohol mole ratio of 1.0) while agitating the mixture and maintaining its temperature between 15° – 20° C. Linear alkylbenzene comprised of a mixture of ($C_{12}$ – $C_{14}$ alkyl) benzenes having random internal isomer distribution is added to the chloromethylation reagent while stirring and maintaining the temperature between 20° – 50° C. After addition of the alkylbenzene is complete (mole ratio of formaldehyde to alkylbenzene is about 1.3) the mixture is maintained at 35° – 45° C. with agitation for 90 minutes to allow completion of the reaction.

The product obtained is alkylbenzyl chloride containing chloromethyl ether impurities.

The product admixed with an amount of 5% aqueous solution of sodium hydroxides sufficient to render the entire mixture alkaline, heated to 70° C. and vigorously agitated.

An alkylbenzyl chloride product layer is separated from the aqueous phase. Conventional analysis indicates that the alkylbenzyl chloride is free from chloromethyl ether impurities.

What is claimed is:

1. A process for removal of chloromethyl ether impurities from alkylbenzyl chlorides containing said impurities and having at least 9 carbon atoms in the alkyl group of the alkylbenzyl moiety, said process comprising contacting said alkylbenzyl chlorides containing said impurities with an aqueous solution of inorganic base selected from the group consisting of alkali metal hydroxides, carbonates and bicarbonates at a temperature of at least 25° C. but below a temperature at which substantial amounts of said chloromethyl ether impurities are volatilized from said alkylbenzyl chloride.

2. The process of claim 1 wherein said inorganic base is sodium hydroxide.

3. The process of claim 2 wherein the aqueous solution of sodium hydroxide contains from 0.1% to 50% by weight sodium hydroxide and an amount of solution containing an amount of sodium hydroxide at least stoichiometrically sufficient to react with all chloromethyl ether impurities present is utilized.

4. The process of claim 3 further comprising separating alkylbenzyl chloride substantially free from chloromethyl ether impurities from an aqueous phase containing products of the reaction between said inorganic base and said impurities.

* * * * *